United States Patent [19]

Sauer et al.

[11] 4,077,996
[45] Mar. 7, 1978

[54] PROCESS FOR THE PREPARATION OF TRANS-DECA HYDRONAPHTHALENE DERIVATIVES

[75] Inventors: Gerhard Sauer; Ulrich Eder; Gregor Haffer; Günter Neef; Rudolf Wiechert, all of Berlin, Germany

[73] Assignee: Schering Aktiengesellschaft, Berlin and Bergkamen, Germany

[21] Appl. No.: 676,805

[22] Filed: Apr. 14, 1976

[30] Foreign Application Priority Data

Apr. 14, 1975 Germany .............................. 2516544

[51] Int. Cl.² ................. C07C 120/00; C07C 121/46; C07D 319/02; C07D 319/04
[52] U.S. Cl. ............................... 260/464; 260/340.7; 260/340.9 AS; 260/410; 260/448.8 R; 260/465 D; 260/586 F; 560/126; 560/256; 560/107
[58] Field of Search ............... 260/464, 586 R, 468 G, 260/586 F, 488 B, 340.7, 340.9

[56] References Cited

U.S. PATENT DOCUMENTS 3,816,536   6/1974   Eder et al. ........................ 260/586 F
3,839,453  10/1974   Eder et al. ........................ 260/586 F

OTHER PUBLICATIONS

Fieser & Fieser, "Reagents for Organic Synthesis", vol. 3, 1972, (pp. 310-311).
Fieser & Fieser, "Reagents for Organic Synthesis", vol. 5, 1975, (pp. 462-463).

Primary Examiner—Joseph Paul Brust
Attorney, Agent, or Firm—Millen & White

[57] ABSTRACT

A process for the preparation of trans-decahydronaphthalene compounds of Formula I

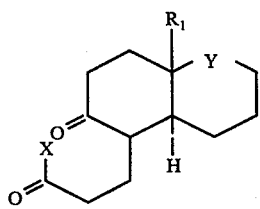

wherein X is lower alkyl, $-(CH_2)_3-Z-R_2$,

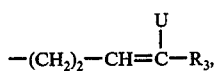

$-(CH_2)_3COOR_4$, or $-(CH_2)_3CN$;
Y and Z are ketalized carbonyl or free, esterified, or etherified hydroxymethylene;
U is halogen;
$R_1$, $R_2$, and $R_3$ are lower alkyl; and
$R_4$ is alkyl;

wherein an octahydronaphthalene compound of Formula II

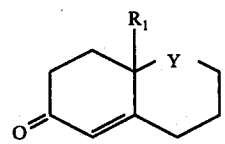

is converted, in the presence of bases, by reaction of a trialkyl chlorosilane of the formula

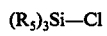

wherein the $R_5$ each are lower alkyl group, to a hexahydronaphthalene compound of the formula

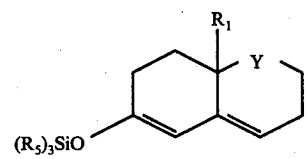

The hexahydronaphthalene compound is hydrogenated, in an inert solvent with hydrogen in the presence of a platinum-, palladium-, or rhodium-containing hydrogenation catalyst, to an octahydronaphthalene compound of the formula

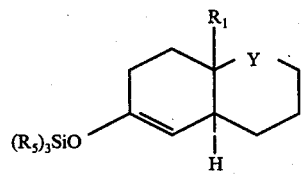

and a vinyl ketone of the formula

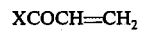

is added to the thus-obtained octahydronaphthalene compound in an inert solvent in the presence of a Lewis acid.

20 Claims, No Drawings

PROCESS FOR THE PREPARATION OF TRANS-DECA HYDRONAPHTHALENE DERIVATIVES

BACKGROUND OF THE INVENTION

This invention relates to the preparation of trans-decahydronaphthalene compounds, which are known or are homologs of conventional 7aβ-alkyl-perhydroindan-5-one derivatives. They are utilized for the total synthesis of pharmacologically active D-homo steroids, including 19-nor-D-homo-testosterone, D-homo-19-norandrost-4-en-3,17a-dione, 3-oxo-D-homo-21,24-dinor-17aα-chol-4-en-23,17a-lacton, 17aα-tert-butoxy-D-homoostr-4-en-3-one.

Compounds of Formula I can be made by condensing octahydronaphthalene derivatives of Formula II with a vinyl ketone of the formula $XCOCH=CH_2$ and hydrogenating the resulting compounds of Formula VII

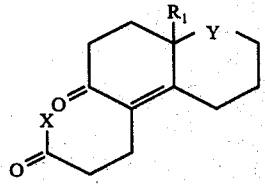

wherein X, Y, and $R_1$ are as above.

However, the vinyl ketone is not selectively added to the double bond, especially if X is lower alkyl. Also, hydrogenation of the compounds of Formula VII does not take place stereospecifically, so that also undesired isomeric compounds are formed in addition to the compounds of Formula I.

To avoid these disadvantages, processes have been suggested for the preparation of compounds of Formula I which make it possible to effect selective alkylation and hydrogenation, but which are rather expensive because of the large number of steps in the synthesis. See, DOS's (German Unexamined Laid-Open Applications) 1,950,012; published Apr. 9, 1970 2,130,053; published Dec. 14, 1972 2,160,066; published June 7, 1973 2,228,473; published Dec. 20, 1973 2,228,474 published Dec. 20, 1973 and 2,228,475 published Dec. 20, 1973.

The process of this invention provides for the synthesis of compounds of Formula I in high yields and high purity in a simple manner.

SUMMARY OF THE INVENTION

This invention relates to a process for preparing a trans-decahydronaphthalene compound of Formula I

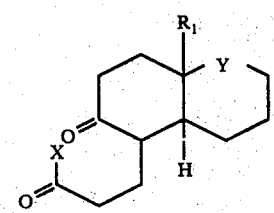

wherein X is alkyl of 1-4 carbon atoms, $-(CH_2)_3-Z-R$,

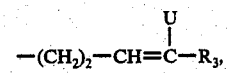

$-(CH_2)_3COOR_4$, or $-(CH_2)_3CN$:

Y and Z is a ketalized carbonyl or free, esterified, or etherified hydroxymethylene;
U is halogen;
$R_1$, $R_2$ and $R_3$ are alkyl of 1-4 carbon atoms; and
$R_4$ is alkyl of 1-10 carbon atoms;
comprising the steps of:
(a) reacting an octahydronaphthalene compound of Formula II

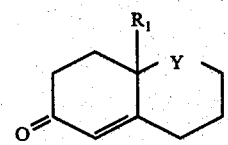

in the presence of bases, with a trialkyl chlorosilane of Formula III

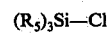

wherein $R_5$ are alkyl of 1-4 carbon atoms to produce a hexahydronaphthalene compound of Formula IV

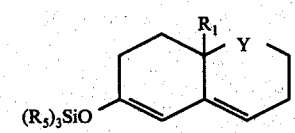

(b) hydrogenating the thus-produced hexahydronaphthalene compound in an inert solvent with hydrogen in the presence of a platinum-, palladium-, or rhodium-containing hydrogenation catalyst, to an octahydronaphthalene compound of Formula V

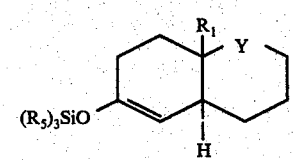

and (c) adding a vinyl ketone of Formula VI

to the thus-produced octahydronaphthalene compound in an inert solvent in the presence of Lewis acids.

DETAILED DESCRIPTION

X, $R_1$, $R_2$, $R_3$ and $R_5$ are alkyl, preferably of 1-4 carbon atoms. Examples of preferred alkyl are: methyl, ethyl, propyl, butyl, and tert.-butyl. Especially preferred alkyl X, $R_1$, $R_2$, and $R_3$ are methyl and ethyl.

$R_4$ are alkyl of 1-10 carbon atoms, preferably alkyl of 1-6 carbon atoms, e.g., methyl, ethyl, propyl, isopropyl, butyl, tert.-butyl, pentyl, hexyl.

Y and Z can be ketalized carbonyl group or free, esterified, or etherified hydroxymethylene group. Ketalized carbonyl include, but are not limited to, alkylenedioxymethylene of 1-6 carbon atoms in the alkylene, e.g., 1,2-ethylenedioxymethylene, 1,3-propylenedioxymethylene, 2,3-butylenedioxymethylene, 2',2'-dimethyl-1',3'-propylenedioxymethylene, 2,4-pentylenedioxymethylene or 1,2-phenylenedioxymethylene. Of these, 1,2-ethylenedioxymethylene and o-phenylenedioxymethylene are preferred.

Esterified hydroxymethylene Y or Z include the alkanoyl or aroyl of up to 10, preferably, up to 6 carbon atoms. Suitable ester residues include, for example, acetoxy, propionyloxy, butyryloxy, trimethylacetoxy, pentanoyloxy, hexanoyloxy, heptanoyloxy, octanoyloxy, and benzoyloxy. Etherified hydroxymethylene groups Y or Z are preferably alkoxymethylene of 1-6 carbon atoms in the alkoxy, e.g., methoxy, ethoxy, propoxy, butoxy, tert.-butyoxy, and isopropoxy.

Preferred halogen U are chlorine and bromine.

Of the processes of this invention, those which are preferred are those directed to compounds of Formula I, wherein:

(a) X is alkyl of 1-4 carbon atoms;
(b) X is —(CH$_2$)$_3$—Z—R$_2$ and Z is alkylenedioxymethylene wherein alkylenedioxy is of 1-6 carbon atoms preferably one with 2-3 carbon atoms in the —O—alkylene—O— chain;
(c) X is —(CH$_2$)$_3$—Z—R$_2$ and Z is o-phenylenedioxymethylene;
(d) X is —(CH$_2$)$_3$—Z—R$_2$ and Z is hydroxymethylene;
(e) X is —(CH$_2$)$_3$—Z—R$_2$, Z is alkanoyl- or aroyloxymethylene and alkanoyl and aroyl each are of up to 10 carbon atoms;
(f) X is —(CH$_2$)$_3$—Z—R$_2$ wherein Z is alkoxymethylene and alkoxy is up to 6 carbon atoms;

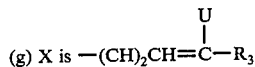

(g) X is —(CH)$_2$CH=C—R$_3$ and U is chlorine or bromine;

(h) X is —(CH$_2$)$_3$COOR$_4$;
(i) X is —(CH$_2$)$_3$CN;
(j) Y is alkylenedioxymethylene and alkylene is of 1-6 carbon atoms, preferably one with 2-3 carbon atoms in the —O—alkylene—O— chain, including (a) - (i);
(k) Y is hydroxymethylene, including (a) - (i);
(l) Y is alkanoyl- or aroylhydroxymethylene and alkanoyl or aroyl each are of up to 10 carbon atoms, including (a) - (i);
(m) Y is alkoxymethylene and alkoxy is of up to 6 carbon atoms, including (a) - (i); and
(n) Y is o-phenylenedioxymethylene, including (a) - (i).

The first step of the process of this invention is conducted under conditions customarily employed for the silylation of oxo compounds.

Thus, octahydronaphthalene derivatives of Formula II are converted to the corresponding enolates in an inert solvent with an alkali hydride, for example, lithium hydride, sodium hydride, or potassium hydride; an alkaline earth hydride, e.g., calcium hydride, or an alkali amide, e.g., lithium amide, sodium amide, or potassium amide and the enolate solutions are treated with a trialkyl chlorosilane of Formula III. Exemplary of inert solvents for this reaction are ethers, e.g., diethyl ether, but preferably tetrahydrofuran, dioxane, and glycol dimethyl ether: dipolar aprotic solvents, e.g., dimethylformamide and hexamethylphosphoric triamide; and tertiary amines, e.g., triethylamine and diisopropylethylamine.

Enolization of compounds of Formula II is accomplished, depending on the enolizing agent, at a reaction temperature of −20° to 120° C. Subsequent silyl ether formation takes place preferably at a temperature of −70° to +20° C.

The first reaction step can also be conducted by reacting the octahydronaphthalene derivatives of Formula II with the desired trialkylchlorosilane in a tertiary amine, e.g., triethylamine, diisopropylethylamine, or 4-dimethylaminopyridine. In this reaction, the tertiary amine can be utilized as the solvent. It is also possible to effect this reaction using additional solvents, e.g., chlorinated hydrocarbons such as chloroform, methylene chloride, and tetrachloroethane; ethers, such as diethyl ether, tetrahydrofuran, dioxane, or glycol dimethyl ether; or dipolar aprotic solvents, such as dimethylformamide, dimethyl sulfoxide, N-methylpyrrolidone, or hexamethylphosphoric triamide.

The reaction is preferably conducted at a temperature of 20°-150° C.

In the second step of the process of the present invention, a hexahydronaphthalene compound of Formula IV is hydrogenated in an inert solvent with hydrogen in the presence of hydrogenation catalysts containing platinum, palladium, or rhodium. Suitable inert solvents for this reaction include, but are not limited to hydrocarbons, such as cyclohexane, benzene, toluene, or xylene; chlorinated hydrocarbons, such as chloroform, methylene chloride, carbon tetrachloride, or tetrachloroethylene; ethers, such as diethyl ether, diisopropyl ether, dioxane, tetrahydrofuran, or glycol dimethyl ether; esters, such as ethyl acetate; or dipolar aprotic solvents, such as dimethylformamide or hexamethylphosphoric triamide. Suitable hydrogenation catalysts are, for example, 5% or 10% palladium-animal charcoal catalyst; 10% palladium-barium sulfate catalyst; 5% or 10% palladium-calcium carbonate catalyst; platinum black catalyst; Adam's catalyst (platinum(IV) oxide); 5% or 10% rhodium-charcoal catalyst; and 5% or 10% rhodium-aluminum oxide catalyst.

The hydrogenation is preferably accomplished at a temperature of 0° to 80° C. under a hydrogen pressure of 1-100 atmospheres.

It is also possible to produce the octahydronaphthalene compounds of Formula V directly from compounds of Formula II, for example, by reacting compounds of Formula II with lithium in liquid ammonia and treating the thus-obtained enolates with trialkyl chlorosilanes. Because this direct reaction is very expensive commercially, the one-step reaction is less advantageous than the two-step procedure.

In the third step of the process of this invention, compounds of Formula V are reacted in an inert solvent in the presence of Lewis acids with a vinyl ketone of Formula VI. Suitable inert solvents for this step are, for example, hydrocarbons, such as hexane or octane; chlorinated hydrocarbons, such as methylene chloride, chloroform, carbon tetrachloride, tetrachloroethylene or chlorobenzene; ethers, such as diethyl ether, diisopropyl ether, tetrahydrofuran, dioxane, or glycol dimethyl ether; dipolar aprotic solvents, such as dimethylformamide or hexamethylphosphoric triamide; and mixtures of the aforementioned solvents. Exemplary of Lewis acids suitable for these reactions are hydrogen chloride, aluminum chloride, boron trifluoride, iron(III) chloride, zinc(II) chloride, zinc acetate, antimony(V)

fluoride, antimony(V) chloride, titanium(IV) chloride, lithium bromide, magnesium bromide, and magnesium perchlorate. The reaction is conducted, depending on the type of Lewis acid employed, at a reaction of −80° to +100° C.

To avoid premature cleavage of the silyl ethers, the three reaction steps are conducted in anhydrous and alcohol-free solvents. During the alkylation reaction and/or working up of the alkylation products, the silyl ethers are cleaved to ketones. If the cleavage is incomplete, the reaction can be finished by heating the products of the process in aqueous or alcohol-containing solvents, optionally with the addition of acids.

If the compounds of formula II contain a free hydroxy group, the latter is silylated during the first reaction step. After the alkylation has been effected, these silyl groups are split off.

The decahydronaphthalene derivatives of general Formula I are valuable intermediates for the total synthesis of pharmacologically active D-homo steroids. Using the same steps utilized for the preparation of pharmacologically effective steroids from conventional 7aβ-alkyl-perhydroindan-5-one derivatives, decahydronaphthalene compounds of Formula I can be converted to pharmacologically active D-homo steroids.

Pharmacologically effective D-homo steroids generally have effects similar to those of the structurally analogous steroids. However, the D-homo steroids frequently have a higher intensity of effectiveness and a more favorable dissociation between desired activity and undesirable side effects than the analogous naturally-occurring steroids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The following examples serve to explain the process of this invention

EXAMPLE 1

(a) 660 mg. of an 85% oily suspension of sodium hydride is washed free of oil with pentane and then added to a solution of 4.76 g. of 1β-tert.-butoxy-8aβ-methyl-1,2,3,4,6,7,8,8a-octahydronaphthalen-6-one. The mixture is heated under argon to 50° C. for 16 hours, then cooled to +5° C., and combined with 5.0 ml. of distilled trimethylchlorosilane. After 15 minutes, 40 ml. of cooled, saturated sodium bicarbonate solution is added to the reaction mixture, and the latter is extracted with cooled pentane, the extract is concentrated, and the yield is 4.95 g. of 1β-tert.-butoxy-8aβ-methyl-6-trimethylsilyloxy-1,2,3,7,8,8a-hexahydronaphthalene as an oily crude product.

IR band at 6.0 μ. UV absorption: $\epsilon_{242}$ = 18,000.

(b) 3.08 g. of 1β-tert.-butoxy-8aβ-methyl-6-trimethylsilyloxy-1,2,3,7,8,8a-hexahydronaphthalene is dissolved in 20 ml. of absolute benzene, combined with 300 mg. of 5% palladium-animal charcoal, and hydrogenated for 3 hours at room temperature under normal pressure. The catalyst is filtered off, the filtrate is concentrated, and the product is 3.1 g. of 1β-tert.-butoxy-8aβ-methyl-6-trimethylsilyloxy-1,2,3,4,4aα,7,8,8a-octahydronaphthalene in the form of an oil.

IR band at 6.02 μ.

(c) 3.10 g. of 1β-tert.-butoxy-8aβ-methyl-6-trimethylsilyloxy-1,2,3,4,4aα,7,8,8a-octahydronaphthalene is dissolved in 10 ml. of methyl chloride, cooled to −78° C., and combined in succession with 1.8 g. of titanium tetrachloride in 5 ml. of methylene chloride and 2.3 g. of 7,7-o-phenylenedioxy-1-octen-3-one in 5 ml. of methylene chloride. The mixture is allowed to stand for 30 minutes, then combined with an aqueous potassium carbonate solution, the precipitate is filtered off, and the filtrate is extracted with methylene chloride. The methylene chloride phase is washed with water, dried over sodium sulfate, and concentrated under vacuum. The residue is purified by chromatography over a silica gel column with hexane-ethyl acetate, thus obtaining 4.2 g. of 1β-hydroxy-8aβ-methyl-5-(7',7'-phenylenedioxy-3'-oxo-octyl)-perhydronaphthalen-6-one as a colorless oil.

IR bands at 5.8 and 6.72 μ.

EXAMPLE 2

(a) 4.4 g. of 1,1-ethylenedioxy-8aβ-methyl-1,2,3,4,6,7,8,8a-octahydronaphthalen-6-one is combined with 16 ml. of triethylamine, 16 ml. of trimethylchlorosilane, and 20 ml. of dimethylformamide, and refluxed for 16 hours. The reaction mixture is then cooled to about 5° C., combined with 40 ml. of ice-cold sodium bicarbonate solution, extracted with pentane, and the extract concentrated under vacuum, thus obtaining 4.6 g. of 1,1-ethylenedioxy-8aβ-methyl-6-trimethylsilyloxy-1,2,3,7,8,8a-hexahydronaphthalene as a colorless oil.

IR band at 6.0 μ. UV extinction $\epsilon_{242}$ = 17,600.

(b) A solution of 2.9 g. of 1,1-ethylenedioxy-8aβ-methyl-6-trimethylsilyloxy-1,2,3,7,8,8a-hexahydronaphthalene in 10 ml. of absolute dimethylformamide is combined with 90 mg. of 10% palladium-animal charcoal and hydrogenated at room temperature and under normal pressure until 250 ml. of hydrogen has been absorbed. The mixture is then separated from the catalyst by filtration, combined with ice-cold water, extracted with pentane, the extract is concentrated under vacuum, and the thus-obtained product is 2.6 g. of 1,1-ethylenedioxy-8aβ-methyl-6-trimethylsilyloxy-1,2,3,4,4aα,7,8,8a-octahydronaphthalene as an oil.

IR band at 6.02 μ.

(c) A solution of 2.60 g. of tin(IV) chloride in 10 ml. of tetrachloromethane is cooled to −20° C. and combined in succession with a solution of 2.96 g. of 1,1-ethylenedioxy-8aβ-methyl-6-trimethylsilyloxy-1,2,3,4,4aα,7,8,8a-octahydronaphthalene in 10 ml. of tetrachloromethane and a solution of 1.6 g. of 5'-oxo-6-heptenoic acid methyl ester in 5 ml. of tetrachloromethane. The mixture is agitated for 2 hours at −20° C., then combined with an aqueous potassium carbonate solution, and worked up as described in Example 1(c). The crude product of 4.8 g. is chromatographed on silica gel, thus producing 2.3 g. of 1,1-ethylenedioxy-8aβ-methyl-5-(3-oxo-6-methoxycarbonyl-hexyl)-perhydronaphthalen-6-one in the form of an oil.

IR bands at 5.75 and 5.8 μ.

EXAMPLE 3

(a) 11.1 g. of 1β-acetoxy-8aβ-methyl-1,2,3,4,6,7,8,8a-octahydronaphthalen-6-one is dissolved in 100 ml. of dimethylformamide, 50 ml. of triethylamine, and 30 ml. of trimethylchlorosilane. The mixture is refluxed for 15 hours and, after cooling, combined with ice-cold buffer solution, pH 6, and extracted three times with cold pentane. The organic phase is dried with sodium sulfate, filtered, and a yield of crude product of 22 g. is thus obtained after the solvent has been distilled off. The crude product is distilled under vacuum (0.12 torr, 160° C., with the use of a bulb tube), thus obtaining 13.2 g. of 1β-acetoxy-8aβ-methyl-6-trimethylsilyloxy-1,2,3,7,8,8a-hexahydronaphthalene.

UV $\epsilon_{239}$ = 16,300. IR: 5.75 μ, 6.05 μ, 6.15 μ.

(b) 12.4 g. of 1β-acetoxy-8aβ-methyl-6-trimethylsilyloxy-1,2,3,7,8,8a-hexahydronaphthalene is dissolved in 420 ml. of toluene, combined with 1.26 g. of palladium/charcoal, and hydrogenated until 1330 ml. of hydrogen has been absorbed. The mixture is then vacuum-filtered off from the catalyst, the solvent is distilled off under vacuum, and the residue is distilled with the aid of a bulb tube at 0.2 torr and 160° C. Yield: 12.1 g. of 1β-acetoxy-8aβ-methyl-6-trimethylsilyloxy-1,2,3,4,4aα,7,8,8a-octahydronaphthalene.

IR: 5.75 μ, 6.0 μ.

(c) 3.6 g. of titanium tetrachloride is dissolved in 40 ml. of methylene chloride; the solution is cooled to −78° C. and mixed with 0.81 ml. of methyl vinyl ketone in 15 ml. of methylene chloride. Then, 3.0 g. of 1β-acetoxy-8aβ-methyl-6-trimethylsilyloxy-1,2,3,4,4aα,7,8,8a-octahydronaphthalene, dissolved in 15 ml. of methylene chloride, is added to the reaction mixture, and the latter is stirred for another 15 minutes at −78° C. The mixture is then poured into 100 ml. of 5% potassium carbonate solution and repeatedly extracted with ether. The ether phases are dried with sodium sulfate, the solvent is evaporated, and the oily residue is distilled under vacuum with the use of a bulb tube (0.2 torr, 160° C.). Yield: 3.3 g. of 1β-acetoxy-5-(3-oxobutyl)-8aβ-methylperhydronaphthalen-6-one.

IR: 5.8 μ, 8.0 μ.

EXAMPLE 4

3.6 g of titanium tetrachloride is dissolved in 40 ml. of methylene chlorid; the solution is cooled to −78° C and mixed with 1.6 g of 7-chlor-1,6-octadien-3-one in 10 ml. of methylene chloride. Then 3.0 g of 1β-acetoxy-8aβ-methyl-6-trimethylsilyloxy-1,2,3-4,4aα7,8,8a-octahydronaphthalene, dissolved in 10 ml. of methylene chloride, is added to the reaction mixture. The mixture is stirred for 2 hours at −78° C and worked up as described in example 3(c). Yield: 4,1 g of oily 1β-acetoxy-5-(7-chloro-3-oxo-6-octen-1-yl)-8a:-methylperhydronaphthalen-6-one.

IR: 6.0 μ, 5.8 μ, 8.0 μ.

EXAMPLE 5

A solution of 2.7 g of aluminum chloride in 20 ml. of methylene chloride is cooled to −78° C and combined in succession with a solution of 2.3 g of 7,7-phenylenedioxy-1-octen-3-one in 15 ml. of methylene chloride and a solution of 3.0 g of 1:-acetoxy-8aβ-methyl-6-trimethylsilyloxy-1,2,3,4,4aα,7,8,8a-octahydronaphthalene in 15 ml. of methylene chloride. The mixture is agitated for 30 minutes at −78° C and then worked up as described in example 3(c). The crude product is distilled under vacuum, thus obtaining of 4.5 g. of 1β-acetoxy-8aβ-methyl-5-(7,7-phenlenedioxy-3-oxo-octyl)-perhydronaphthalene as an oil.

IR: 5.75 μ, 5.8 μ, 6.75 μ.

EXAMPLE 6

3.6 g of titanium tetrachloride is dissolved in 20 ml. of chloroform; the solution is cooled to −60° C and mixed with 1.7 g of the ethylester of 5-keto-6-heptenoic acid in 10 ml chloroform. Then 3.0 g of 1β-acetoxy-8a:-methyl-6-trimethylsilyloxy-1,2,3,4,4aα,7,8,8a-octahydronaphthalene, dissolved in 10 ml. of chloroform, is added to the reaction mixture. The mixture is stirred for 30 minutes at −60° C and worked up as described in example 3(c). Yield: 3.9 g of ethyl ester of 7-(1β-acetoxy-8aβ-methyl-6-oxo-perhydronaphthalen-5-yl)-5-oxoheptanoic acid as an oil.

IR: 5.75 μ, 5.8 μ.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a trans-decahydronaphthalene compound of the formula

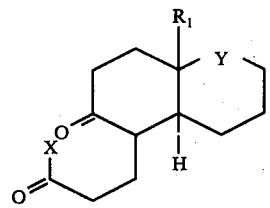

wherein X is alkyl of 1-4 carbon atoms, —(CH$_2$)$_3$—Z—R$_2$

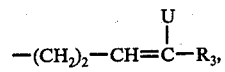

—(CH$_2$)$_3$COOR$_4$, or —(CH$_2$)$_3$CN;

Y and Z are alkylenedioxymethylene of up to 6 carbon atoms in the alkylene, hydroxymethylene, alkanoyloxymethylene or aroyloxymethylene of up to 10 carbon atoms in the alkanoyl or aroyl or alkoxymethylene of up to 6 carbon atoms in the alkoxy;

U is chlorine or bromine;

R$_1$, R$_2$, and R$_3$ are alkyl of 1-4 carbon atoms; and

R$_4$ is alkyl of 1-10 carbon atoms; comprising the steps of:

(a) reacting an octahydronaphthalene compound of the formula

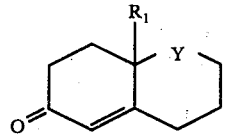

in the presence of a base, with a trialkyl chlorosilane of the formula

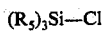

wherein R$_5$ is alkyl of 1-4 carbon atoms, to produce a hexahydronaphthalene compound of the formula

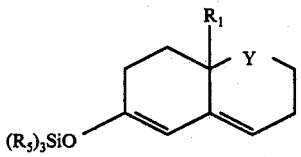

(b) hydrogenating the thus-produced hexahydronaphthalene compound in an inert solvent with hydrogen in the presence of a platinum-, palladium-, or rhodium-containing hydrogenation catalyst, to an ocathydronaphthalene compound of the formula

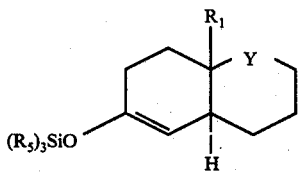

and (c) reacting a vinyl ketone of the formula

XCOCH=CH$_2$ with the thus-produced octahydronaphthalene compound in an inert solvent in the presence of a Lewis acid; wherein all three reaction steps are conducted in anhydrous, alcohol-free solvents.

2. The process of claim 1, wherein X is alkyl of 1-4 carbon atoms.

3. The process of claim 1, wherein X is —(CH$_2$)$_3$—Z—R$_2$.

4. The process of claim 3, wherein Z is alkylenedioxymethylene and alkylene is of up to 6 carbon atoms with 2-3 carbon atoms in the chain linking the oxygen atoms.

5. The process of claim 3, herein Z is o-phenylenedioxymethylene.

6. The process of claim 3, wherein Z is hydroxymethylene.

7. The process of claim 3, wherein Z is alkanoyl or aroyloxymethylene and alkanoyl and aroyl each are of up to 10 carbon atoms.

8. The process of claim 3, wherein Z is alkoxymethylene and alkoxy is of up to 6 carbon atoms.

9. The process of claim 1, wherein X is

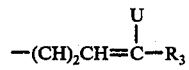

and U is chlorine or bromine.

10. The process of claim 1, wherein X is —(CH$_2$)$_3$—COOR$_4$.

11. The process of claim 1, wherein X is —(CH$_2$)$_3$CN.

12. The process of claim 1, wherein Y is alkylenedioxymethylene and alkylene is of up to 6 carbon atoms with 2-3 carbon atoms in the chain linking the oxygen atoms.

13. The process of claim 1, wherein Y is hydroxymethylene.

14. The process of claim 1, wherein Y is alkanoyl- or aroyloxymethylene and alkanoyl or aroyl are each of up to 10 carbon atoms.

15. The process of claim 1, wherein Y is alkoxymethylene and alkoxy is of up to 6 carbon atoms.

16. The process of claim 1, wherein Y is o-phenylenedioxymethylene.

17. The process of claim 1, wherein the octahydronaphthalene compound is converted to an enolate prior to reaction with the trialkyl chlorosilane.

18. The process of claim 1, wherein the octahydronaphthalene compound is reacted with the trialkyl chlorosilane in a tertiary amine.

19. The process of claim 1, wherein the Lewis acid is titanium tetrachloride.

20. The process of claim 1, wherein the Lewis acid is tin(IV) chloride.

* * * * *